| United States Patent [19] | [11] Patent Number: 4,830,966 |
| --- | --- |
| Close | [45] Date of Patent: * May 16, 1989 |

[54] PROCESS FOR REGENERATING CORN

[75] Inventor: Kelly R. Close, Woodside, Calif.

[73] Assignees: Sungene Technologies Corporation; Sungenetics, Inc., both of San Jose, Calif.; Sunagra Research, Reno, Nev.

[*] Notice: The portion of the term of this patent subsequent to May 12, 2004 has been disclaimed.

[21] Appl. No.: 865,431

[22] Filed: May 21, 1986

Related U.S. Application Data

[63] Continuation-in-part of Ser. No. 648,389, Sep. 7, 1984.

[51] Int. Cl.$^4$ ............................................. C12N 5/00
[52] U.S. Cl. ........................... 435/240.49; 435/240.5; 435/240.51; 435/240.54
[58] Field of Search ........... 435/240.49, 240.5, 240.54, 435/172.2, 240.51; 47/58; 800/1

[56] References Cited

U.S. PATENT DOCUMENTS 4,665,030  5/1987  Close ................................... 435/240

FOREIGN PATENT DOCUMENTS 0177738  4/1986  European Pat. Off. .
2539579  7/1984  France .

OTHER PUBLICATIONS

Green, C. E., et al., *Crop Science* 15, 417 (1975).
Freeling, M., et al., *Maydica* 21, 97 (1976).
Lu, C., et al., *Theor. Appl. Genet.* 66, 285 (1983).
Edallo, S., et al. *Maydica* 26, 39 (1981).
Hibberd, K. A., et al., *Proc. Natl. Acad. Sci. USA* 79, 559 (1982).
Gengenbach, B. G., et al., *Proc. Natl. Acad. Sci. USA* 74, 5113 (1977).
Green, C. E., et al., *Crop Science* 14, 54 (1974).
Duncan et al., *Planta* 165, 322 (1985).
Irvine, J. E., et al., *Plant Cell Tissue Organ Culture* 2, 141 (1983).
Hanning, G. E., et al., *Theor. Appl. Genet.* 63, 15 (1982).
Conger, B. V., et al., *Science* 221, 850 (1983).
Conger, B. V., et al., *Crop Science* 18, 157 (Jan.–Feb. 1978).
Vasil, *Cell Culture and Somatic Cell Genetics of Plants, I*, 19, 1984.
Conger, B. V., *Cloning Argicultural Plants Via In Vitro Techniques* 113, 175 (1981).

*Primary Examiner*—Charles F. Warren
*Assistant Examiner*—David T. Fox
*Attorney, Agent, or Firm*—Robbins & Laramie

[57] ABSTRACT

The present invention relates to the regeneration of corn. The process comprises the steps of:
(a) culturing tissue obtained from a corn plant on a first medium which comprises mineral salts, vitamins sucrose and a hormone for callus formation;
(b) subculturing the calli on a second medium which comprises mineral salts, vitamins, sucrose and a hormone for callus maintenance;
(c) subculturing the calli on a third medium which comprises mineral salts, vitamins, sucrose and optionally a hormone for shoot and root formation; and
(d) optionally subculturing said shoots on a fourth medium which comprises mineral salts, vitamins, sucrose and optionally a hormone for plantlet maturation including additional root formation, whereby plants are obtained.

32 Claims, No Drawings

PROCESS FOR REGENERATING CORN

This application is a continuation-in-part of copending application Ser. No. 648,389, filed Sept. 7, 1984.

BACKGROUND OF THE INVENTION

1. Field of the Invention

The present invention relates to a general process for regenerating corn and to plants produced by the process. More particularly, the present invention relates to the use of tissue and cell culture for the regeneration or corn plantlets from many varieties of corn.

2. Description of the Prior Art

Plant regeneration from cells in culture is essential for the application of somatic hybridization, for the production of new varieties through somaclonal variation and for the use of genetic engineering in producing new varieties. Although plants can be regenerated from tissue culture of several varieties of corn, there are many varities for which this has not been accomplished using similar techniques.

In recent years, plant cell culture successes have had a considerable influence on the respective roles of cell and organism in control of plant growth and development. This concept was supported when isolated plant cells were shown to be amenable to in vitro cultivation and complete plants could be regenerated from cultures derived from somatic tissues, either directly via somatic embryogenesis or indirectly via organogenesis. Generally the regeneration pathway of choice is determined empirically by the manipulation of extrinsic factors, especially growth regulators. Early investigations of certain plant species have suggested that exogenous auxin concentration is a major factor controlling somatic embryogenesis, such that its reduction leads to the initiation of embryoid formation. In other species, exposure to a definite balance of auxin and cytokinin leads to the occurrence of organogenesis (shoots, then roots). Although several genotypes of corn have been regenerated using these techniques, no process is generally applicable to most genotypes of corn. Many genotypes remain extremely difficult if not impossible to culture using the prior processes.

The process which has become the standard system for corn tissue culture is described by Green et al., *Crop Science* 15, 417 (1975). In this process, immature embryos were plated onto a callus induction medium which comprises the MS mineral salts, Straus vitamins and amino acids (glycine, asparagine, niacin, thiamine, pyridoxine and pantothenic acid), 2% sucrose, 0.8% agar and a hormone selected from 2,4-dichlorophenoxyacetic acid (2,4-D), p-chlorophenoxyacetic acid (PCA), alphanaphthaleneacetic acid (NAA), 2-isopentyladenine (2-ip) or mixtures thereof. Plantlets were regenerated by subculturing the callus on medium containing reduced hormone concentrations. Hormone concentrations which were useful were 2 mg/l 2,4-D and a mixture of 1 mg/l 2,4-D, 4 mg/l NAA and 0.05 mg/l 2-ip. Regeneration was then accomplished on medium containing 0.25 mg/l 2,4-D or a mixture of 1 mg/l NAA and 0.05 mg/l 2-ip respectively. All culturing was conducted in a 16 hour light/8 hour dark cycle for 3-4 week intervals before transfer. This reference reports that callus induction did not occur in one of five genotypes tested.

Similar results have been reported by others. Freeling et al., *Maydica* 21, 97 (1976) obtained regeneration of corn by utilizing a sequence of callus induction on a RM medium containing 2 or 5 mg/l 2,4-D, 2% sucrose and no myo-inositol followed by regeneration on the same medium with 0-0.1 mg/l,2,4-D. Vasil et al., *Theor. Appl. Genet.* 66, 285 (1983) obtained callus formation and shoot formation after 3 weeks of culturing when utilizing a MS medium containing 3-12% sucrose and 0.25-2.0 mg/l 2,4-D. High sucrose concentration was most favorable for embryogenic callus. Root formation was accomplished after transfer to (a) MS medium with 3% sucrose with or without 1 mg/l fiberellic acid (GA$_3$) or (b) ½ MS medium with 2% sucrose.

Edallo et al., *Maydica* 26, 39 (1981) obtained callus induction from immature corn embryos using the medium of Green et al., supra, with 2 mg/l 2,4-D. The culture could be maintained on the same medium with 30 day transfers. Regeneration was accomplished by using medium with no 2,4-D. Shoots were transferred to medium having a 1 mm overlayer of 5 mg/l NAA for root formation. Prior to transferring the plantlets to soil, they were cycled through media having 2%, 1% and finally 0% sucrose. Regeneration of corn plants using a similar sequence of callus induction with 2,4-D and regeneration with no or low 2,4-D has been shown by Lu et al., *Theor. Appl. Genet.* 62, 109 (1982); Hibberd et al., *Proc. Natl. Acad. Sci. USA* 79, 559 (1982); Gegenbach et al., *Proc. Natl. Acad. Sci. USA* 74, 5113 (1977); and Green et al., *Crop Science* 14, 54 (1974). The latter reference also demonstrates genotype affects on callus induction.

None of this prior art describes a process for the regeneration of most genotypes of corn *Zea mays* from tissue and cell culture. Examples of cultivars that cannot be regenerated or can only be regenerated with great difficulty at low frequency by these prior art processes include B73, A632, A619, CM105, B37, B84, B14, Mo17 and R168. The present invention is the first instance of a broadly and generally applicable procedure for regenerating cultivars of corn with a high frequency and with a high growth rate.

Duncan et al. *Planta* 165, 322 (1985) has demonstrated that, in accordance with the present invention, many cultivars of corn can be regenerated using dicamba as the hormone in the callus induction medium. Duncan et al. utilized different media combinations of mineral salts and vitamins to obtain these results.

Corn plants and seeds are produced by this process. The corn plants resulting from this process may differ from the starting plant material as a result of somaclonal variation. The pathway is also useful in that it will enable the use of various selection processes to provide further variation. The plants which are produced can be used in conventional breeding programs.

SUMMARY OF THE INVENTION

The process of the present invention comprises the steps of inducing callus formation on an induction medium from tissue of a corn plant, maintaining the calli, forming shoots and roots on a regeneration medium and optionally maturing the plantlets on a maturation medium.

More specifically, the present process comprises the steps of:

(a) culturing tissue obtained from a corn plant on a first medium which comprises mineral salts, vitamins sucrose and a hormone in an amount sufficient to ensure callus formation;

(b) subculturing the calli on a second medium which comprises mineral salts, vitamins, sucrose and a hormone in an amount sufficient to ensure callus maintenance;

(c) subculturing the calli on a third medium which comprises mineral salts, vitamins, sucrose and optionally a hormone in an amount sufficient to ensure shoot formation and root formation; and (d) optionally subculturing said shoots on a fourth medium which comprises mineral salts, vitamins, sucrose and optionally a hormone in an amount sufficient to ensure plantlet maturation including additional root formation, whereby plants are obtained.

The source of the tissue is preferably immature embryos from cultivars of Zea mays. The media preferably contain N6 mineral salts and modified MS vitamins. The preferred hormones are 3,6-dichloro-2-methoxybenzoic acid (dicamba) or 3-amino-2,5-dichlorobenzoic acid (chloramben) in the first, second and third media and dicamba, chloramben or a mixture of either dicamba or chloramben and 2,4-D in the fourth medium.

DETAILED DESCRIPTION OF THE INVENTION

The present invention is directed to a process for regenerating corn, Zea mays, through the use of cell or tissue culture. In this process, regenerated corn plantlets are obtained which can be placed in soil and grown to maturation. The present invention is also directed to corn plants obtained by this process and seeds obtained from these plants.

In general, the process comprises (a) culturing corn plant tissue on a medium to produce calli, (b) culturing the calli on a medium to maintain the calli, (c) culturing the calli on a medium to produce shoots and roots, and (d) optionally culturing the shoots with roots on a medium to mature the plantlets for transplanting. After plantlets have been developed, they can be grown in soil.

The plant tissue which is preferred for use in the initiation of callus is the immature embryo. The immature embryos are isolated from the cob at approximately 10 days post-pollination when the embryos are 1.5–2.0 mm in length. The cob is harvested and surface sterilized. The immature embryos are isolated from each kernel. The embryos are plated onto callus induction medium, hereinafter referred to as the first medium, so that the embryo axis is in contact with the medium, i.e. the scutellar side is up.

The first medium comprises mineral salts, vitamins and sucrose. The mineral salts comprise macroelements and microelements. The macroelements used in the first medium may be combinations of the following compounds: magnesium sulfate, calcium chloride, monopotassium phosphate, potassium nitrate, ammonium nitrate, and ammonium sulfate. The microelements contained in the first medium are combinations of: boric acid, manganese sulfate, zinc sulfate, potassium iodide, iron (II) sulfate, disodium-ethylenediamine tetracetic acid (EDTA), sodium EDTA ferric salt, sodium molybdate (VI), copper (II) sulfate and cobalt chloride. Several combinations of mineral salts may be used as long as they do not adversely affect callus induction. Examples of combinations of mineral salts include but are not limited to MS, modified MS, N6, modified N6, Heller, Nitsch and Nitsch, B5 and White, and combinations thereof. Some examples of mineral salt combinations are disclosed in Duncan et al., supra.

One preferred combination of the macroelements and microelements are N6 salts. One liter of these salts is prepared from the following: 185 mg magnesium sulfate heptahydrate, 166 mg calcium chloride dihydrate, 400 mg monopotassium phosphate, 2830 mg potassium nitrate, 463 mg ammonium sulfate, 1.6 mg boric acid, 3.3 mg manganese sulfate monohydrate, 1.5 mg zinc sulfate heptahydrate, 0.8 mg potassium iodide, 27.8 mg iron (II) sulfate heptahydrate, and 37.3 mg disodium-EDTA.

Another, more preferred, combination of the macroelements and microelements are modified N6 salts. These salts are identical to the above described salts, but additionally include, per one liter of medium, 0.25 mg sodium molybdate (VI) dihydrate, 0.025 mg copper (II) sulfate pentahydrate and 0.025 mg cobalt chloride hexahydrate.

Yet another preferred combination of the macroelements and microelements are the MS salts which comprise, per one liter of medium, the following: 370 mg magnesium sulfate heptahydrate, 440 mg calcium chloride dihydrate, 170 mg monopotassium phosphate, 1900 mg potassium nitrate, 1650 mg ammonium nitrate, 6.2 mg boric acid, 15.6 mg manganese sulfate monohydrate, 8.6 mg zinc sulfate heptahydrate, 0.83 mg potassium iodide, 27.8 mg iron (II) sulfate heptahydrate, 37.3 mg disodium-EDTA, 0.25 mg sodium molybdate (VI) dihydrate, 0.025 mg copper (II) sulfate pentahydrate and 0.025 mg cobalt chloride hexahydrate.

Another preferred combination of macroelements and microelements, hereinafter referred to as "N6 macro/B5 micro", comprises 185 mg magnesium sulfate heptahydrate, 166 mg calcium chloride dihydrate, 400 mg monopotassium phosphate, 2830 mg potassium nitrate, 463 mg ammonium sulfate, 3 mg boric acid, 10 mg manganese sulfate monohydrate, 2 mg zinc sulfate heptahydrate, 0.75 mg potassium iodide, 0.25 mg sodium molybdate (VI) dihydrate, 0.025 mg copper (II) sulfate pentahydrate, 0.025 mg cobalt chloride heptahydrate, and 43 mg EDTA sodium ferric salt.

The first medium also contains vitamins. Combinations of the following vitamins may be used: myo-inositol, nicotinic acid, aminobenzoic acid, cyanocobalamin, pyrodoxine, folic acid, thiamine, choline, riboflavin, biotin, and pantothenate.

A preferred combination of vitamins are modified MS vitamins which comprise, per one liter of the first medium, 100 mg myo-inositol, 0.5 mg nicotinic acid, 2 mg glycine, 0.5 mg pyridoxine hydrochloride and 0.1 mg thiamine hydrochloride and 0.25 mg calcium pantothenate.

Another preferred combination of vitamins are the RT vitamins. This combination comprises, per liter of medium, 0.70 $\mu$M choline hydrochloride, 0.13 $\mu$M riboflavin, 0.41 $\mu$M D-biotin, 0.11 $\mu$M folic acid, 1.62 $\mu$M nicotinic acid, 0.30 $\mu$M thiamine hydrochloride, 0.21 $\mu$M calcium pantothenate, 0.97 $\mu$M pyridoxine hydrochloride, 0.10 nM cyanocobalamin, and 0.36 $\mu$M p-aminobenzoic acid.

Still another preferred combination are the N6 vitamins. This combination comprises, per one liter of medium, 1 mg thiamine hydrochloride, 0.5 mg pyridoxine hydrochloride, and 0.5 mg nicotinic acid.

Preferred combinations of macroelements, microelements and vitamins are summarized in the following Table:

| SUMMARY OF MEDIA USED FOR CALLUS INDUCTION | | | | | |
| --- | --- | --- | --- | --- | --- |
| | A | B | C | D | E |
| macronutrients | N6 | N6 | MS | N6 | N6 |
| micronutrients | modified N6 | N6 | MS | B5 | N6 |
| vitamins | modified MS | modified MS | modified MS | RT | N6 |

The first medium contains 1.5–12% sucrose, preferably 9%. It is also possible to substitute some of the sucrose with mannitol. A gelling agent such as agar or Gelrite ™ (trademark, Kelco Commercial Development, P.O. Box 23076, San Diego, Calif.) is also contained in the medium. It is preferred to use Gelrite ™ at a concentration of 0.18%. The medium has a pH of 5.5–6.0 with a preferred pH of 5.8. Additional optional components of the media include NaFeEDTA, L-proline, enzymatic casein hydrolysate, casamino acids, glucose, potassium nitrate, and thiamine hydrochloride.

In addition to the above components, the first medium also contains a hormone. As used herein, hormone is intended to mean any natural or synthetic compound which has a regulatory effect on plants or plant tissue. Plant hormones include auxins and cytokinins. It has been found that the hormone which is useful for callus induction in the present invention is of formula I

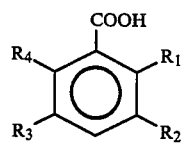

wherein $R_1$ and $R_3$ are identical and are selected from the group comprising F, Cl, Br and I; $R_2$ is selected from the group comprising $NH_2$, $NO_3$, OH, Cl and H, and $R_4$ is selected from the group comprising Cl, $OCH_3$ and H. Preferably, $R_1$ and $R_3$ are both Cl or are both Br.

The amount of hormone present is sufficient to ensure callus formation. Generally, 5–60 μM, preferably 5–30 μM, is sufficient. It is most preferred to use 5–30 μM chloramben (i.e., $R_1$ and $R_3$ are Cl, $R_2$ is $NH_2$, and $R_4$ is H) as the hormone in the first medium. It has also been found that the use of abscisic acid (ABA) increases the frequency of callus induction at 2–3% sucrose. 0.1–2.0 μM, preferably 0.1–1.0 μM may be utilized. The medium is sterilized by autoclaving all of the components except the vitamins and the hormone. The latter are sterilized by microporous membrane filtration prior to addition to the autoclaved medium.

When chloramben is utilized as the hormone, it has been found that 80–100% initiation frequency is possible for the following genotypes: A188, A619, A632, B14, B37, B68, B73, B84, B79, C103, CM105, H98, Mo17, MS71, R168, Va26, Va59, Wf9, W64A, W117, and W182Bn.

The immature embryos are plated on the first medium and cultured in diffused light with a photoperiod of 16 hours per day for 2–4 weeks, preferably 2–3 weeks. During this time, the embryo undergoes de-differentiation and callus formation. After culturing the immature embyro on the first medium, the callus is transferred and subcultured on a maintenance medium, hereinafter referred to as the second medium. The callus is subcultured on the second medium is diffused light for 4–8 weeks. The callus can be maintained on the second medium for a longer period of time if desired. After 2–4 weeks, the callus is transferred to a fresh second medium. Any roots which have formed are removed at each transfer of the callus.

The second medium comprises mineral salts, vitamins, sucrose and a hormone in an amount sufficient to maintain the callus. The mineral salts, vitamins, and hormone are chosen from those described for the first medium. The mineral salts, vitamins, and hormone used in the second medium may be the same or different as the first, preferably, the same medium is used. As in the first medium, various combinations of mineral salts which do not adversely affect the functioning of the medium may be utilized. The sucrose concentration is 1.5–6%, preferably 3%. The hormone is of the same general formula I as the one employed in the first medium. Preferably the hormone is chloramben or dicamba (i.e., $R_1$ and $R_3$ are chloro, $R_2$ is hydrogen, and $R_4$ is $OCH_3$). Generally, 5–15 μM, preferably 5–10 μM is sufficient. Most preferably, chloramben is used in the amount of 5–10 μM, with 5 μM preferred. Gelrite ™ is added to the medium to solidify it. A concentration of 0.18% is satisfactory. The medium has a pH of 5.5–6.0 with 5.8 preferred. The medium is sterilized as described above.

The sucrose concentration for maintenance can be dropped to the desired level immediately or in a stepwise manner. For example, callus from first medium containing 9% sucrose can be transferred to second medium containing 3% sucrose. Alternatively, it can first be transferred to second medium containing 6% sucrose and cultured for 2–4 weeks and then transferred to second medium having 3% sucrose.

It may also be desirable to add ABA to the second medium to slow down the growth of the tissue. This is preferred for long term maintenance of the callus. When ABA is utilized, 0.1–2.0 μM, preferably 0.1–1.0 μM is used.

After culturing the callus on the second medium, it is transferred and subcultured on a regeneration medium, hereinafter referred to as the third medium and cultured in diffused light. The third medium may contain the same or different mineral salts and vitamins as the first medium. Preferably, the same medium is used. As in the first medium, various combinations of mineral salts which do not adversely affect the functioning of the medium may be utilized. In addition, this medium may contain a hormone to ensure shoot formation. It has been found that the hormone of the same general formula I as employed in the first and second media, either alone or in admixture with 2.4-D (i.e., 2,4-dichlorophenoxyacetic acid), is useful for shoot and root formation. The 2,4-D may be added to promote root formation. Generally, 0–5 μM, preferably 1 μM of a hormone of formula I alone or in combination with 0–0.1 μM 2,4-D is utilized. It is preferred to use chloramben if any hormone is present.

It is preferred that the third medium contains 1.5–6% sucrose, preferably 3%, and the same amount of gelling substance as the first medium and has the same pH. This medium is also sterilized by autoclaving and membrane filtration as previously described.

In order to enhance the efficiency of plant regeneration on the third medium, it may be desirable to first transfer the maintained callus to fresh second medium having a higher sucrose concentration for 1–2 weeks before transferring it to the third medium. For example, if the callus is being maintained on second medium having 3% sucrose, the callus could first be transferred to fresh second medium having 6% sucrose before being transferred to the third medium.

Once shoots and roots have formed, they can be transferred to soil or they can optionally be transferred to a maturation medium, hereinafter referred to as the fourth medium, and cultured in diffused light. The fourth medium is identical to the third medium except that it contains 1-3%, preferably 2% sucrose. It is preferred that no hormone be utilized in this medium. If one is present, then 0-1.0 µM of a hormone of formula I, and preferably dicamba or chloramben, with or without 0-0.1 µM 2,4-D, may be used.

After roots have formed, the plantlets are ready to be transferred to soil. Shoots having well established roots are removed from the tubes and the Gelrite ™ washed off. The plants are transplanted to soil having two parts potting soil and one part vermiculite and kept moist in a high humidity chamber. The plants are then transplanted to larger pots.

This process is useful for regenerating plantlets from tissue of many cultivars of corn. It is especially useful for regenerating plantlets from cultivars for which prior art methods have been unsuccessful to regenerate plants. Examples of these cultivars include B73, A632, CM105, B37, B84, B14, Mo17, R168. In addition to these cultivars, the present process is also useful to regenerate cultivars which have previously been regenerated by prior techniques. Examples of these cultivars include MS71, A188, PA91, A641, W117.

The primary difficulty with prior art systems for regenerating various cultivars of corn has been the inability to induce callus formation. In general, if a callus could be induced from corn tissue, the callus could then be processed to regenerate plants. Thus, the ability to induce callus formation is the step which limits the regeneration of several cultivars of corn. The present invention discloses a method for inducing callus formation and plant regeneration. The method of regenerating plants is applicable to all cultivars of corn once callus tissue has been formed. Consequently, in the examples which follow, the general procedure has been shown for several cultivars of corn including B73, B37, A619, A632, Mo17 and MS71. The callus for each cultivar had the same general appearance as did the callus from B73. Consequently, plants can be obtained from each of these cultivars by following the procedure described herein.

The present invention will be further described by reference to the following non-limiting examples. In these examples, culturing in the light refers to culturing an diffused light having a photoperiod of 16 hours per day at 25° C. unless indicated otherwise. The temperature during the 8 hours park phase is 25° C. unless indicated otherwise.

EXAMPLE 1

Preparation of Solutions

The following stock solutions or solutions were prepared for use in making the media described in further detail below.

1. Mineral Salts

A. Monopotassium phosphate

A 200× stock solution was prepared by dissolving 8 g of monopotassium phosphate in 100 ml of distilled deionized water. The stock solution was stored in the refrigerator.

B. Remaining mineral salts

A 10× stock solution was prepared by dissolving 7.40 g magnesium sulfate heptahydrate, 6.64 g calcium chloride dihydrate, 113.2 g potassium nitrate, 18.52 g ammonium sulfate, 64 mg boric acid, 132 mg manganese sulfate monohydrate, 60 mg zinc sulfate heptahydrate, 33.2 mg. potassium iodide, 10 mg sodium molybdate (VI) dihydrate, 1.0 mg copper (II) sulfate pentahydrate and 1.0 mg cobalt chloride hexahydrate in 3600 ml of distilled, deionized water. 1.112 g of iron (II) sulfate heptahydrate and 1.492 g of disodium-EDTA were individually dissolved in 200 ml of distilled, deionized water by heating and were then mixed together slowly with stirring. This mixture was then added to the remainder of the salts. The salts stock solution was divided into 100 ml aliquots and frozen until used.

2. Vitamins

A 100× stock solution of vitamins was prepared by dissolving 10 g myo-inositol. 50 mg of nicotinic acid, 200 mg glycine, 50 mg pyridoxine hydrochloride, 100 mg thiamine hydrochloride and 25 mg calcium pantothenate in 100 ml of distilled, deionized water, which was then diluted ten fold with distilled, deionized water to prepare the stock solution. 100 ml aliquots were frozen in dark bottles until used.

3. Hormones

A. Dicamba A.

A 1 mg/ml stock solution was prepared by diluting 0.21 ml of dicamba obtained from Velsicol Chemicals to 100 ml with distilled deionized water. This solution was stored in the refrigerator.

B. 2,4-D

A 0.5 mM stock solution was prepared by dissolving 11.05 mg of 2,4-D in 0.5-1.0 ml of 1.0N KOH and diluting to 100 ml with distilled, deionized water. The pH was adjusted to 5.8 with 1.0N HCl, and the solution was stored in the refrigerator.

C. Chloramben

A 0.55 mM stock solution was prepared as described for 2,4-D using 10.30 mg of chloramben.

D. Dicamba B.

A 0.55 mM stock solution was prepared as described for 2,4-D using 11.05 mg of dicamba.

E. Others

A 0.5 mM stock solution of each of the other hormones described herein was prepared in a similar manner as described for 2,4-D by using the appropriate amount of the hormone.

EXAMPLE 2

Preparation of Media

1. First Medium or Callus Induction Medium

The first medium was prepared by adding 40 g of sucrose and 100 ml of the 10× mineral stock solution to 800 ml of distilled, deionized water. 5 ml of the 200× monopotassium phosphate stock solution was then added and the volume brought to one liter with distilled, deionized water. The pH was adjusted to 5.95 with 1.0N KOH. The pH was adjusted high to compensate for the approximate 0.15 drop which normally occurs during autoclaving. 1.8 g of Gelrite ™ was added and the mixture autoclaved for 15 minutes at 15 psi. 10 ml of the 100× vitamin stock solution and 2 ml of the dicamba A stock solution were sterilized by filtration through a 0.2µ Gelman filter and then added to the cooling medium which was then poured into petri dishes or test tubes.

To prepare first medium having a different concentration of dicamba, the appropriate amount of the stock solution was used. For example, to prepare a first medium having 3 mg/l dicamba, 3 ml of the dicamba stock solution was used or if 10 μM is desired, then 20 ml of the dicamba B stock solution is used.

To prepare first medium having a different hormone, the appropriate amount of the hormone stock solution was used. For example, to prepare first medium having 10 μM chloramben, 20 ml of the chloramben stock solution was used.

2. Second Medium or Maintenance Medium

The second medium was prepared as described above for the first medium except that 1 ml of the dicamba A stock solution was utilized. Second medium having other concentrations of dicamba were prepared as described above. Second medium having a different hormone was prepared in the analogous manner as described above.

3. Third Medium or Regeneration Medium

The third medium was prepared as described above for the first medium except (a) 0.1 ml of the dicamba stock solution was used and (b) 0.2 ml of the 2,4-D stock solution was added to the media after the addition of the 200× monopotassium phosphate stock solution. To prepare thirdmedium having different concentrations of hormones, containing different hormones or containing only dicamba or chloramben or a mixture of dicamba and chloramben, the appropriate amounts of the stock solutions were added as previously described.

4. Fourth Medium or Maturation Medium

The fourth medium was prepared as described above for the first medium except (a) 20 g of sucrose and (b) 0.1 ml of the dicamba stock solution were used. Fourth medium having a different concentration of dicamba or having a different hormone chloramben was prepared as described above. Fourth medium having a hormone of formula I in combination with 2,4-D was prepared in the analogous manner as for the third medium.

EXAMPLE 3

Corn Regeneration

Immature embryos were isolated from cobs of corn Zea mays L. B73, B37, A632, A619, Mo17 or MS71 10-11 days post-pollination when they were 1.5 mm in length. Each cob was harvested and surface sterilized in a solution containing 30% Clorox ® (Clorox Company, Oakland, Calif.) bleach (1.6% sodium hypochlorite) and 1-2 drops/200 ml of Liquinox ® (Alconox Inc., 853 Broadway, New York, N.Y.) detergent for 15 minutes. The cobs were rinsed with sterile, deionized water four times. The immature embryos were isolated by slicing off the top of each kernel with a scalpel and scooping out the endosperm. The immature embryos are then taken out and plated onto the first medium, contained in a petri dish, so that the embryo axis was in contact with the medium, i.e. the scutellar side was up. The first medium was prepared as described in the preceding example using either 2 mg/l dicamba or 2 mg/l chloramben. The petri dish was placed in the light and cultured for 4 weeks.

At this time, each callus was transferred to the second medium, which was prepared as described above, using 1 mg/l of either dicamba or chloramben, and also contained in a petri dish. The callus was cultured on this medium for 6 weeks in the light with transfer to fresh medium after three weeks. At each transfer, any roots which had formed were removed from each callus.

Each callus was then transferred to the third medium. The third medium was prepared as described in Example 2, using 0.1 mg/l of either dicamba or chloramben and 0.1 μM 2,4-D. The callus was cultured on this medium in the light for 5 days. The callus differentiated to form shoots and roots.

The shoots with roots were then transferred to the fourth medium, contained in culture tubes. The fourth medium was prepared as described above, using 0.1 mg/l of either dicamba or chloramben. The shoots with roots were cultured in the light for 1-2 weeks during which additional roots formed.

The plantlets were transferred to soil in the greenhouse. Shoots with well established roots were removed from the tubes and the Gelrite ™ was thoroughly washed off with tap water. The plantlets were placed in potting cubes containing two parts potting soil and one part vermiculite. The potting cubes were placed in a high humidity chamber and kept moist for five days. The lid of the chamber was then removed. After three more days the plants were transplanted to 12" pots. The plants were watered 2-3 times per week and fertilized every two weeks. Plants were obtained from each cultivar from each regeneration sequence using either dicamba or chloramben.

EXAMPLE 4

Corn Regeneration

Immature embryos were isolated from the following cultivars of corn and plated onto first medium as described in Example 3: Zea mays L. A632, A619, CM105, B37, B84, B14, M017, R168, MS71, A641 and W117 except sucrose concentration was either 3% or 9%. Callus was obtained and had the same or better general appearance as the callus of Example 3 for each cultivar. Following the general procedure of Example 3, plants were obtained for cultivars A632, A619, B37, B84, Mo17, MS71 and A641. Plants could be obtained in the same general manner for the other cultivars.

EXAMPLE 5

Corn Regeneration

Immature embryos were isolated from Zea mays L. B73 and MS71 as described in Example 3. The embryos were plated onto first medium containing 10 μM chloramben or 10 μM dicamba and either (a) 3%, (b) 6%, (c) 9% or (d) 12% sucrose. Callus was obtained and had the same general appearance as the callus of Example 3 in each instance except for B73 on 3% sucrose. First medium having 9% or 12% sucrose was found to be better for callus induction. Following the general procedure of Example 3, plants were obtained for each cultivar using either chloramben or dicamba.

EXAMPLE 6

Corn Regeneration

Immature embryos were isolated as described in Example 3 from the corn cultivars identified in Examples 3 and 4. The embryos were plated onto first medium containing 10 μM chloramben or 10 μM dicamba and either 9% or 3% sucrose. Callus was obtained and had the same general appearance as the callus of Example 3 for each cultivar except B73 on 3% sucrose. Following the general procedure of Example 3, plants were obtained using either chloramben or dicamba.

EXAMPLE 7

Corn Regeneration

Following the procedure of Examples 3–6, callus was initiated from immature embryos of *Zea mays* B73, B37, and MS 71 cultivars on media containing the following amounts of hormones (in $\mu M$):

| Hormone | B73 | B37 | MS 71 |
|---|---|---|---|
| 2,5 dichlorobenzoic acid | 5–15 | 5–15 | 10 |
| 2,5 dibromobenzoic acid | 10 | 10 | 10 |
| 3-amino-2,5-dichlorobenzoic acid | 5–60 | 5–60 | 5–60 |
| 3-nitro-2,5-dichlorobenzoic acid | 5–15 | 5–15 | 10–20 |
| 2,3,5-trichlorobenzoic acid | 5–15 | 5–15 | 10 |
| 2-methoxy-3,6-dichlorobenzoic acid | 5–60 | 5–60 | 5–60 |

With the exception of the B73 and B37 cultivars in the presence of 3-nitro-2,5-dichloro benzoic acid, callus was obtained for each cultivar at the concentration of hormone given. Following the general procedure of Example 3, plants were obtained for each cultivar.

EXAMPLE 8

Corn Regeneration

Following the procedure of Examples 3–6, callus was initiated from immature embryos of *Zea mays* B73, B84, Mo17, A619, MS71, and Pa91 and plants were regenerated on medium which contained MS mineral salts instead of modified N6 mineral salts.

EXAMPLE 9

Corn Regeneration

Following the procedure of Examples –6, callus was initiated from immature embryos of *Zea mays* B73, B84, Mo17, A619, MS71, C103, B37, Pa91, and Oh 43 and plants were regenerated on medium which contained N6 mineral salts instead of modified N6 mineral salts.

While the invention has been described in connection with specific embodiments thereof, it will be understood that it is capable of further modifications. This application is intended to cover any variations, uses or adaptations of the invention following, in general, the principles of the invention and including such departures from the present disclosure as come within known and customary practice within the art to which the invention pertains.

What is claimed is:

1. A process for regenerating corn plantlets from cell or tissue which comprises the steps of:
    (a) culturing tissue obtained from a corn plant on a first medium comprising mineral salts, vitamins, sucrose and a hormone selected from the group consisting of (i) a hormone of formula I

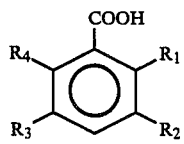

wherein $R_1$ and $R_3$ are identical and are selected from the group consisting of Cl and Br; $R_2$ is selected from the group consisting of $NH_2$, Cl and H; and $R_4$ is selected from the group consisting of Cl, $OCH_3$ and H and (ii) a mixture of a hormone of formula I and ABA for callus formation;
    (b) subculturing said callus on a second medium comprising mineral salts, vitamins, sucrose and a hormone selected from the group consisting of (i) a hormone of formula I and (ii) a mixture of a hormone of formula I and ABA for callus maintenance; and
    (c) subculturing said callus on a third medium comprising mineral salts, vitamins, and sucrose to form shoots and roots, whereby plants are obtained.

2. The process of claim 1 wherein said tissue is obtained from immature embryo.

3. The process of claim 1 wherein said shoots and roots are subcultured on a fourth medium comprising mineral salts, vitamins and sucrose.

4. The process of claim 1 wherein said third medium further comprises a hormone selected from the group consisting of (i) a hormone of formula I and (ii) a mixture of a hormone of formula I and 2,4-D.

5. The process of claim 3 wherein said fourth medium further comprises a hormone selected from the group consisting of (i) a hormone of formula I and (ii) a mixture of a hormone of formula I and 2,4-D.

6. The process of claim 4 wherein said shoots and roots are subcultured on a fourth medium comprising mineral salts, vitamins and sucrose.

7. The process of claim 6 wherein said fourth medium further comprises a hormone selected from the group consisting of (i) a hormone of formula I and (ii) a mixture of a hormone of formula I and 2,4-D.

8. The process of claim 1 wherein the concentrations of said hormones in said media are:
    (1) 5–15 $\mu M$ of said hormone of formula I or a mixture of 5–15 $\mu M$ of said hormone of formula I and 0.1–1.0 $\mu M$ ABA in said first medium; and
    (2) 5–10 $\mu M$ of said hormone of formula I or a mixture of 5–15 $\mu M$ of said hormone of formula I and 0.1–1.0 $\mu M$ ABA in said second medium.

9. The process of claim 4 wherein the concentrations of said hormones in said media are:
    (1) 5–15 $\mu M$ of said hormone of formula I or a mixture of 5–15 $\mu M$ of said hormone of formula I and 0.1–1.0 $\mu M$ ABA in said first medium;
    (2) 5–10 $\mu M$ of said hormone of formula I or a mixture of 5–15 $\mu M$ of said hormone of formula I and 0.1–1.0 $\mu M$ ABA in said second medium; and
    (3) about 0.1–5.0 $\mu M$ of said hormone of formula I or a mixture of about 0.1–5.0 $\mu M$ of said hormone of formula I and about 0.1 $\mu M$ 2,4-D in said third medium.

10. The process of claim 3 wherein the concentration of said hormones in said media are:
    (1) 5–15 $\mu M$ of said hormone of formula I or a mixture of 5–15 $\mu M$ of said hormone of formula I and 0.1–1.0 $\mu M$ ABA in said first medium; and
    (2) 5–10 $\mu M$ of said hormone of formula I or a mixture of 5–15 $\mu M$ of said hormone of formula I and 0.1–1.0 $\mu M$ ABA in said second medium.

11. The process of claim 5 wherein the concentrations of said hormones in said media are:
    (1) 5–15 $\mu M$ of said hormone of formula I or a mixture of 5–15 $\mu M$ of said hormone of formula I and 0.1–1.0 $\mu M$ ABA in said first medium;
    (2) 5–10 $\mu M$ of said hormone of formula I or a mixture of 5–15 $\mu M$ of said hormone of formula I and 0.1–1.0 $\mu M$ ABA in said second medium; and (3) about 0.1–1.0 μM of said hormone of formula I or a mixture of about 0.1–1.0 μM of said hormone of formula I and about 0.1 μM 2,4-D in said fourth medium.

12. The process of claim 6 wherein the concentrations of said hormones in said media are:
(1) 5–15 μM of said hormone of formula I or a mixture of 5–15 μM of said hormone of formula I and 0.1–1.0 μM ABA in said first medium;
(2) 5–10 μM of said hormone of formula I or a mixture of 5–15 μM of said hormone of formula I and 0.1–1.0 μM ABA in said second medium; and
(3) about 0.1–5.0 μM of said hormone of formula I or a mixture of about 0.1–5.0 μM of said hormone of formula I and about 0.1 μM 2,4-D in said third medium.

13. The process of claim 7 wherein the concentrations of said hormones in said media are:
(1) 5–15 μM of said hormone of formula I or a mixture of 5–15 μM of said hormone of formula I and 0.1–1.0 μM ABA in said first medium;
(2) 5–10 μM of said hormone of formula I or a mixture of 5–15 μM of said hormone of formula I and 0.1–1.0 μM ABA in said second medium;
(3) about 0.1–5.0 μM of said hormone of formula I or a mixture of about 0.1–5.0 μM of said hormone of formula I and about 0.1 μM, 2,4-D in said third medium; and
(4) about 0.1–1.0 μM of said hormone of formula I or a mixture of about 0.1–1.0 μM of said hormone of formula I and about 0.1 μM 2,4-D in said fourth medium.

14. The process of claim 1 wherein the concentration of sucrose is:
(1) 1.5–12% in said first medium; and
(2) 1.5–6% in said second and third media.

15. The process of claim 3 wherein the concentration of sucrose is:
(1) 1.5–12% in said first medium;
(2) 1.5–6% in said second and third media; and
(3) 1–3% in said fourth medium.

16. The process of claim 1 wherein the concentration of sucrose is:
(1) 1.5–12% in said first medium;
(2) 1.5–6% in said second and third media; and
(3) 1–3% in said fourth medium.

17. A process for regenerating corn plantlets of the genotype MS71 from cell or tissue culture which comprises the steps of:
(a) culturing tissue obtained from a corn plant on a first medium comprising mineral salts, vitamins, sucrose and a hormone selected from the group consisting of (i) 3-nitro-2,5-dichlorobenzoic acid, and (ii) a mixture of 3-nitro-2,5-dichlorobenzoic acid and ABA;
(b) subculturing said callus on a second medium comprising mineral salts, vitamins, sucrose and a hormone selected from the group consisting of (i) 3-nitro-2,5-dichlorobenzoic acid, and (ii) a mixture of 3-nitro-2,5-dichlorobenzoic acid and ABA;
(c) subculturing said callus on a third medium comprising comprising mineral salts, vitamins, and sucrose to form shoots and roots, whereby plants are obtained.

18. The process of claim 17 wherein said tissue is obtained from immature embyro.

19. The process of claim 17 wherein said shoots and roots are subcultured on a fourth medium comprising mineral salts, vitamins and sucrose.

20. The process of claim 17 wherein said third medium further comprises a hormone selected from the group consisting of (i) 3-nitro-2,5-dichlorobenzoic acid and (ii) a mixture of 3-nitro-2,5-dichlorobenzoic acid and 2,4-D.

21. The process of claim 19 wherein said fourth medium further comprises a hormone selected from the group consisting of (i) 3-nitro-2,5-dichlorobenzoic acid and (ii) a mixture of 3-nitro-2,5-dichlorobenzoic acid and 2,4-D.

22. The process of claim 20 wherein said shoots and roots are subcultured on a fourth medium comprising mineral salts, vitamins and sucrose.

23. The process of claim 22 wherein said fourth medium further comprises a hormone selected from the group consisting of (i) 3-nitro-2,5-dichlorobenzoic acid and (ii) a mixture of 3-nitro-2,5-dichlorobenzoic acid and 2,4-D.

24. The process of claim 17 wherein the concentrations of said hormones in said media are:
(1) 5–15 μM of 3-nitro-2,5-dichlorobenzoic acid or a mixture of 5–15 μM of 3-nitro-2,5-dichlorobenzoic acid and 0.1–1.0 μM ABA in said first medium; and
(2) 5–10 μM of 3-nitro-2,5-dichlorobenzoic acid or a mixture of 5–15 μM of 3-nitro-2,5-dichlorobenzoic acid and 0.1–1.0 μM ABA in said second medium.

25. The process of claim 20 wherein the concentrations of said hormones in said media are:
(1) 5–15 μM of 3-nitro-2,5-dichlorobenzoic acid or a mixture of 5–15 μM of 3-nitro-2,5-dichlorobenzoic acid and 0.1–1.0 μM ABA in said first medium;
(2) 5–10 μM of 3-nitro-2,5-dichlorobenzoic acid or a mixture of 5–15 μM of 3-nitro-2,5-dichlorobenzoic acid and 0.1–1.0 μM ABA in said second medium; and
(3) about 0.1–5.0 μM of 3-nitro-2,5-dichlorobenzoic acid or a mixture of about 0.1–5.0 μM of 3-nitro-2,5-dichlorobenzoic acid and about 0.1 μM 2,4-D in said third medium.

26. The process of claim 19 wherein the concentrations of said hormones in said media are:
(1) 5–15 μM of 3-nitro-2,5-dichlorobenzoic acid or a mixture of 5–15 μM of 3-nitro-2,5-dichlorobenzoic acid and 0.1–1.0 μM ABA in said first medium; and
(2) 5–10 μM of 3-nitro-2,5-dichlorobenzoic acid or a mixture of 5–15 μM of 3-nitro-2,5-dichlorobenzoic acid and 0.1–1.0 μM ABA in said second medium.

27. The process of claim 21 wherein the concentrations of said hormones in said media are:
(1) 5–15 μM of 3-nitro-2,5-dichlorobenzoic acid or a mixture of 5–15 μM of 3-nitro-2,5-dichlorobenzoic acid and 0.1–1.0 μM ABA in said first medium;
(2) 5–10 μM of 3-nitro-2,5-dichlorobenzoic acid or a mixture of 5–15 μM of 3-nitro-2,5-dichlorobenzoic acid and 0.1–1.0 μM ABA in said second medium; and
(3) about 0.1–1.0 μM of 3-nitro-2,5-dichlorobenzoic acid or a mixture of about 0.1–1.0 μM of 3-nitro-2,5-dichlorobenzoic acid and about 0.1 μM 2,4-D in said fourth medium.

28. The process of claim 22 wherein the concentrations of said hormones in said media are:
(1) 5–15 μM of 3-nitro-2,5-dichlorobenzoic acid or a mixture of 5–15 μM of 3-nitro-2,5-dichlorobenzoic acid and 0.1–1.0 μM ABA in said first medium;

(2) 5–10 μM of 3-nitro-2,5-dichlorobenzoic acid or a mixture of 5–15 μM of 3-nitro-2,5-dichlorobenzoic acid and 0.1–1.0 μM ABA in said second medium; and (3) about 0.1–5.0 μM of 3-nitro-2,5-dichlorobenzoic acid or a mixture of about 0.1–5.0 μM of 3-nitro-2,5-dichlorobenzoic acid and about 0.1 μM 2,4-D in said third medium.

29. The process of claim 23 wherein the concentrations of said hormones in said media are:
(1) 5–15 μM of 3-nitro-2,5-dichlorobenzoic acid or a mixture of 5–15 μM of 3-nitro-2,5-dichlorobenzoic acid and 0.1–1.0 μM ABA in said first medium;
(2) 5–10 μM of 3-nitro-2,5-dichlorobenzoic acid or a mixture of 5–15 μM of 3-nitro-2,5-dichlorobenzoic acid and 0.1–1.0 μM ABA in said second medium;
(3) about 0.1–5.0 μM of 3-nitro-2,5-dichlorobenzoic acid or a mixture of about 0.1–5.0 μM of 3-nitro-2,5-dichlorobenzoic acid and about 0.1 μM 2,4-D in said third medium; and
(4) about 0.1–1.0 μM of 3-nitro-2,5-dichlorobenzoic acid or a mixture of about 0.1–1.0 μM of 3-nitro-2,5-dichlorobenzoic acid and about 0.1 μM 2,4-D in said fourth medium.

30. The process of claim 1 wherein the concentration of sucrose is:
(1) 1.5–12% in said first medium; and
(2) 1.5–6% in said second and third media.

31. The process of claim 19 wherein the concentration of sucrose is:
(1) 1.5–12% in said first medium;
(2) 1.5–6% in said second and third media; and
(3) 1–3% in said forth medium.

32. The process of claim 22 wherein the concentration of sucrose is:
(1) 1.5–12% in said first medium;
(2) 1.5–6% in said second and third media; and
(3) 1–3% in said forth medium.

* * * * *